US011530526B2

(12) United States Patent
Elkins

(10) Patent No.: US 11,530,526 B2
(45) Date of Patent: Dec. 20, 2022

(54) SYSTEM AND METHOD FOR PERFORMING AN EARTHMOVING OPERATION

(71) Applicant: CNH Industrial America LLC, New Holland, PA (US)

(72) Inventor: Scott A. Elkins, Homer Glen, IL (US)

(73) Assignee: CNH Industrial America LLC, New Holland, PA (US)

(*) Notice: Subject to any disclaimer, the term of this patent is extended or adjusted under 35 U.S.C. 154(b) by 334 days.

(21) Appl. No.: 16/832,646

(22) Filed: Mar. 27, 2020

(65) Prior Publication Data

US 2021/0301501 A1 Sep. 30, 2021

(51) Int. Cl.
*E02F 9/26* (2006.01)
*E02F 3/43* (2006.01)
*E02F 3/32* (2006.01)

(52) U.S. Cl.
CPC .............. *E02F 9/262* (2013.01); *E02F 3/439* (2013.01); *E02F 3/32* (2013.01)

(58) Field of Classification Search
CPC .............. E02F 3/439; E02F 9/262; E02F 3/32
See application file for complete search history.

(56) References Cited

U.S. PATENT DOCUMENTS

| | | | |
|---|---|---|---|
| 5,704,142 A | 1/1998 | Stump | |
| 8,139,108 B2 | 3/2012 | Stratton et al. | |
| 8,849,523 B1 | 9/2014 | Chan et al. | |
| 10,712,330 B2 * | 7/2020 | Long | G01N 33/2823 |
| 2006/0241838 A1 * | 10/2006 | Mongiardo | B60K 35/00 701/50 |
| 2006/0287792 A1 * | 12/2006 | Jarrett | A01B 79/005 701/50 |
| 2007/0214687 A1 * | 9/2007 | Woon | E02F 3/842 701/50 |

(Continued)

FOREIGN PATENT DOCUMENTS

| | | |
|---|---|---|
| CN | 103650695 B | 6/2016 |
| CN | 109159633 A | 1/2019 |

OTHER PUBLICATIONS

Extended European Search Report for EP Application No. 21165532.9 dated Nov. 5, 2021 (six pages).

*Primary Examiner* — Yazan A Soofi
(74) *Attorney, Agent, or Firm* — Peter Zacharias; Patrick Sheldrake

(57) ABSTRACT

A system for performing an earthmoving operation may include a work vehicle having an articulable implement and a soil composition sensor supported on the work vehicle. The soil composition sensor may generate data indicative of a soil composition below a surface of a worksite. The system may additionally include a computing system communicatively coupled to the soil composition sensor and the work vehicle. The computing system may receive an input associated with a target profile of the worksite. The computing system may further receive the data indicative of the soil composition of the worksite. Additionally, the computing system may generate an earthmoving prescription map based at least in part on the target profile of the worksite and the soil composition of the worksite, where the earthmoving prescription map indicates soil composition layers between the surface of the worksite and the target profile of the worksite.

20 Claims, 4 Drawing Sheets

(56) References Cited

U.S. PATENT DOCUMENTS

| | | | |
|---|---|---|---|
| 2007/0219693 A1* | 9/2007 | Stratton | E02F 9/2029 701/50 |
| 2007/0239337 A1* | 10/2007 | Anderson | A01B 79/005 701/50 |
| 2007/0288147 A1* | 12/2007 | Reeves | A01D 41/1217 701/50 |
| 2012/0136508 A1* | 5/2012 | Taylor | E02F 9/2045 701/25 |
| 2014/0180547 A1* | 6/2014 | Edara | G05D 1/0278 701/50 |
| 2014/0180548 A1* | 6/2014 | Edara | E02F 9/261 701/50 |
| 2014/0277957 A1 | 9/2014 | Clar et al. | |
| 2015/0004572 A1* | 1/2015 | Bomer | G09B 9/042 434/219 |
| 2016/0076223 A1* | 3/2016 | Wei | E02F 3/435 701/50 |
| 2016/0077513 A1* | 3/2016 | Wei | G05D 1/0217 700/114 |
| 2017/0059544 A1 | 3/2017 | Stafford | |
| 2018/0210454 A1* | 7/2018 | Ready-Campbell | E02F 9/2045 |
| 2019/0033441 A1 | 1/2019 | Gonzales Valdes et al. | |
| 2019/0064362 A1 | 2/2019 | Scott | |
| 2020/0063396 A1 | 2/2020 | Ready-Campbell et al. | |
| 2021/0235609 A1* | 8/2021 | Ferrari | G01S 13/885 |
| 2021/0309352 A1* | 10/2021 | Elkins | G01S 13/885 |

\* cited by examiner

SYSTEM AND METHOD FOR PERFORMING AN EARTHMOVING OPERATION

FIELD OF THE INVENTION

The present disclosure relates generally to work vehicles, such as excavators, bull-dozers, graders and backhoes, and, more particularly, to systems and methods for performing an earthmoving operation with a work vehicle based on a soil composition of a worksite.

BACKGROUND OF THE INVENTION

A wide variety of work vehicles, such as excavators, loaders, graders, shovels, bull-dozers, and/or the like, have been developed for performing various tasks of earthmoving operations, such as carrying loads, moving earth, digging, dumping, stockpiling, and/or the like, at a worksite. These work vehicles have implements, such as buckets, claws, and/or the like of varying sizes, which are selected based on the site and task requirements. Typically, a machine operator manually controls the operation of the work vehicle to excavate one soil type at a time for sorting into different piles according to future use. However, such manual operation often results in a larger degree of mixing of the different soil types than desired. Further, the work vehicle operational settings may not be suitable for working all soil types, which may affect the efficiency of the work vehicle and the earthmoving operation.

Accordingly, an improved system and method for performing an earthmoving operation would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a method for performing an earthmoving operation with a work vehicle, where the work vehicle has an articulable implement. The method includes receiving, with a computing device, an input associated with a target profile of a worksite. The method further includes receiving, with the computing device, data indicative of a soil composition of a worksite below a surface of the worksite. Moreover, the method includes generating, with the computing device, an earthmoving prescription map based at least in part on the target profile of the worksite and the soil composition of the worksite, where the earthmoving prescription map indicates soil composition layers between the surface of the worksite and the target profile of the worksite. Additionally, the method includes controlling, with the computing device, an operation of the work vehicle based at least in part on the earthmoving prescription map.

In another aspect, the present subject matter is directed to a system for performing an earthmoving operation, where the system includes a work vehicle having an articulable implement and a soil composition sensor supported on the work vehicle, where the soil composition sensor is configured to generate data indicative of a soil composition below a surface of a worksite. Additionally, the system includes a computing system communicatively coupled to the soil composition sensor and the work vehicle. The computing system is configured to receive an input associated with a target profile of the worksite, receive the data indicative of the soil composition of the worksite, and generate an earthmoving prescription map based at least in part on the target profile of the worksite and the soil composition of the worksite. The earthmoving prescription map indicates soil composition layers between the surface of the worksite and the target profile of the worksite.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
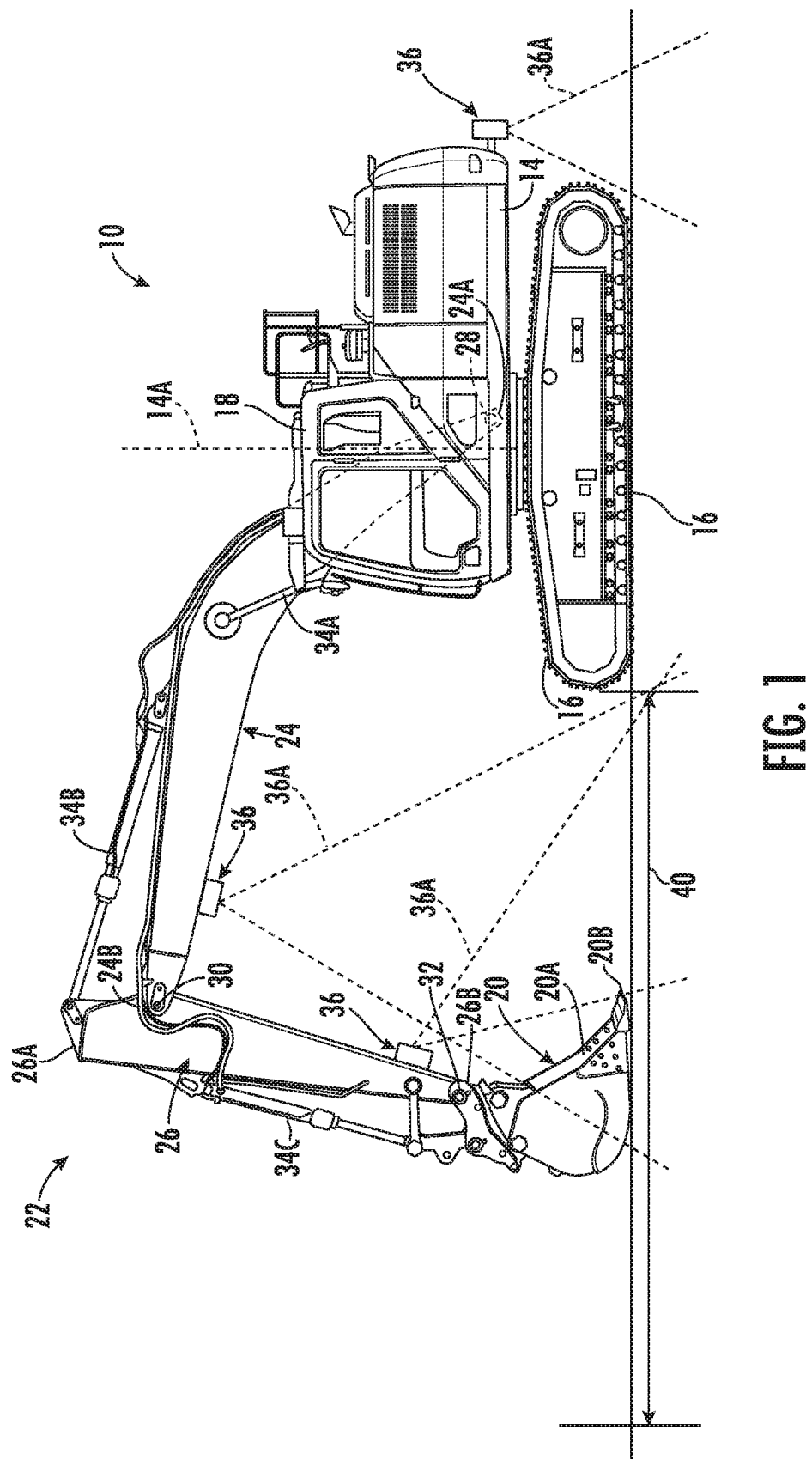
FIG. 1 illustrates a side view of one embodiment of a work vehicle in accordance with aspects of the present subject matter.

Repeat use of reference characters in the present specification and drawings is intended to represent the same or analogous features or elements of the present technology.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for performing an earthmoving operation. Specifically, in several embodiments, the disclosed system includes a work vehicle having an articulable implement, such as a bucket or claw, and a soil composition sensor supported by the work vehicle. The soil composition sensor is configured to detect different soil composition layers beneath a surface of a worksite. A computing system of the disclosed system is configured to generate an earthmoving prescription map based on the soil composition layers and a target profile or grade of the worksite. In particular, the earthmoving prescription map indicates changes between the soil composition layers at different depths between a surface of the worksite and the target grade of the worksite.

In some embodiments, the earthmoving prescription map also prescribes one or more operational settings of the work vehicle for working each soil composition layer. The computing system may control a user interface to indicate to an operator the distance to the next soil composition layer such that the operator can better separate the soil types when stockpiling, and optionally indicate prescribed operational setting(s) of the work vehicle for each soil composition layer such that the work vehicle may be more fuel and time efficient. Additionally, or alternatively, the computing system may be configured to control the work vehicle to automatically perform an earthmoving operation to separate the different soil composition layers based on the earthmoving prescription map.

Referring now to drawings, FIG. 1 illustrates a perspective view of one embodiment of a work vehicle 10. As shown, the work vehicle 10 is configured as an excavator. However, in other embodiments, the work vehicle 10 may be configured as any other suitable work vehicle, such as a loader, shovel, grader, backhoe, bull-dozer, and/or the like.

As shown in FIG. 1, the work vehicle 10 includes a frame or chassis 14 coupled to and supported by a pair of tracks 16 for movement across a worksite. However, in other embodiments, the chassis 14 may be supported in any other way, for example by wheels, a combination of wheels and tracks, or a fixed platform. In some embodiments, an operator's cab 18 may be supported by a portion of the chassis 14 and may house a user interface 60 (FIG. 2) comprising various input devices for permitting an operator to control the operation of one or more components of the work vehicle 10. However, it should be appreciated that, in some embodiments, one or more components of the user interface 60 may be positioned remotely from the work vehicle 10.

Moreover, the work vehicle 10 has drive components (FIG. 2), such as an engine 19A, a transmission 19B, and a differential 19C mounted on the chassis 14. The transmission 19B may be operably coupled to the engine 19A and may provide variably adjusted gear ratios for transferring engine power to the tracks 16 via a drive axle assembly (or via axles if multiple drive axles are employed). The tracks 16 coupled to each axle may be selectively locked together for rotation by the differential 19C coupled to the axle between the tracks 16. Selective coupling or decoupling of the differential 19C allows the work vehicle 10 provides controllable steering to the work vehicle 10.

Additionally, the work vehicle 10 includes an implement 20 articulable relative to the chassis 14 for performing earth moving operations within a worksite. The chassis 14 may, in some embodiments, be configured such that the operator's cab 18 and/or the articulable implement 20 is rotatable about a chassis axis 14A. In one embodiment, the implement 20 is part of a linkage assembly 22 comprising a boom arm 24 and a dipper arm 26. The boom arm 24 extends between a first end 24A and a second end 24B. Similarly, the dipper arm 26 extends between first end 26A and a second end 26B. The first end 24A of the boom arm 24 is pivotably coupled to the chassis 14 about a first pivot axis 28, and the second end 24B of the boom arm 24 is pivotably coupled to the first end 26A of the dipper arm 26 about a second pivot axis 30. Further, the implement 20 is pivotably coupled to the second end 26B of the dipper arm 26 about a third pivot axis 32. The implement 20, in one embodiment, is configured as a bucket having a cavity 20A and a plurality of teeth 20B, where the teeth 20B help to break up worksite materials for collection within the cavity 20A. However, in other embodiments, the implement 20 may be configured as any other suitable ground engaging tool, such as a claw, and/or the like.

The linkage assembly 22 further includes a plurality of actuators for articulating components 20, 24, 26 of the linkage assembly 22. For instance, a first actuator 34A is coupled between the boom arm 24 and the chassis 14 for pivoting the boom arm 24 relative to the chassis 14. Similarly, a second actuator 34B is coupled between the boom arm 24 and the dipper arm 26 for pivoting the dipper arm 26 relative to the boom arm 24. Further, a third actuator 34C is coupled between the dipper arm 26 and the implement 20 (hereafter referred to as "bucket 20" for the sake of simplicity and without intent to limit) for pivoting the bucket 20 relative to the dipper arm 26. In one embodiment, the actuators 34A, 34B, 34C are configured as hydraulic cylinders. However, it should be appreciated that the actuators 34A, 34B, 34C may be configured as any other suitable actuators or combination of actuators. By selectively pivoting the components 24, 24, 26 of the linkage assembly 22, the bucket 20 may perform various earthmoving operations within a worksite. In particular, the bucket 20 may be actuatable over a stroke length 40, where the stroke length 40 generally extends from adjacent the tracks 16 to where the bucket 20 is fully extended away from the cab 18.

As will be described below in greater detail, the actuators 34A, 34B, 34C of the work vehicle 10 may be controlled by a computing system of the disclosed system to perform one or more tasks of an earthmoving operation for a worksite. For instance, the actuators 34A, 34B, 34C of the work vehicle 10 may be used to determine the current fill of the bucket 20 (e.g., based on the force(s) of the actuator(s) used to actuate the bucket 20) and/or the position of the bucket 20 along the stroke length 40 and/or relative to the target profile of the worksite. A maximum bucket fill percentage is typically selected according to the soil type being excavated, with the maximum bucket fill percentage being higher for lighter, easier to work soil types.

It should be appreciated that the position of the bucket 20 along the stroke length 40 and/or relative to the target profile of the worksite may be determined in any other suitable way. For instance, one or more position sensors (not shown) may be positioned on one or more components of the work vehicle 10 for determining and/or monitoring the position of the bucket 20. For example, the position sensor(s) may comprise accelerometer(s), gyroscope(s), inertial measurement unit(s) (IMU(s)), rotational sensor(s), proximity sensor (s), a combination of such sensors, and/or the like.

Still referring to FIG. 1, in accordance with aspects of the present invention, the work vehicle 10 may further include one or more soil composition sensors 36 configured to generate data indicative of a soil composition below a surface of a worksite. For instance, the soil composition sensor(s) 36 (hereafter referred to simply as "sensor(s) 36") may be supported on the operator's cab 18, the bucket 20, and/or the arm(s) 24, 26 such that a field of view 36A of each sensor 36 is directable towards the worksite. In some embodiments, the field of view 36A of the sensor(s) 36 may be directed towards at least a portion of the worksite along the stroke length 40 of the bucket 20. In one embodiment, the field of view 36A of the sensor(s) 36 may be directed towards at least a portion of the worksite outside of the stroke length 40 of the bucket 20. In some embodiments, the sensor(s) 36 are fixed relative to the respective portion of the work vehicle 10 on which it is supported (e.g., the cab 18, the bucket 20, and/or arms 24, 26). However, in other embodiments, the sensor(s) 36 are movable relative to the respective portion of the work vehicle 10 on which it is supported (e.g., the cab 18, the bucket 20, and/or arms 24, 26). More specifically, the sensor(s) 36 may be movable to generate data indicative of the soil composition across a larger portion of the worksite than if the sensor(s) 36 was stationary.

The sensor(s) 36 may be configured as any suitable device or combination of devices for generating such data, such as a ground penetrating radar (GPR). For instance, in embodiments where the sensor(s) 36 comprises a ground penetrating radar or another similar device, the sensor(s) 36 may be configured to generate a polarized field comprised of polarized electromagnetic waves within the field of view 36A of the sensor(s) 36. The polarized field may penetrate the field surface, wherein the reflection of waves within the polarized field may be used to detect various sub-surface soil layers and other sub-surface features, e.g., buried infrastructure (pipes, wires, etc.). For instance, such reflected waves may indicate changes in density below the surface of the worksite, which may further be indicative of changes between different soil types and/or the presence of sub-surface features. Such data (e.g., reflected waves) may be used to generate an earthmoving prescription map for controlling the operation of the bucket 20 during an earth moving operation, as will be described in greater detail below.

It should be appreciated that the configuration of the work vehicle 10 described above and shown in FIG. 1 is provided only to place the present subject matter in an exemplary field of use. Thus, it should be appreciated that the present subject matter may be readily adaptable to any manner of work vehicle configuration. For example, in an alternative embodiment, the work vehicle 10 may further include any other tools, implements, and/or components appropriate for use with a work vehicle 10.

Figure 2:
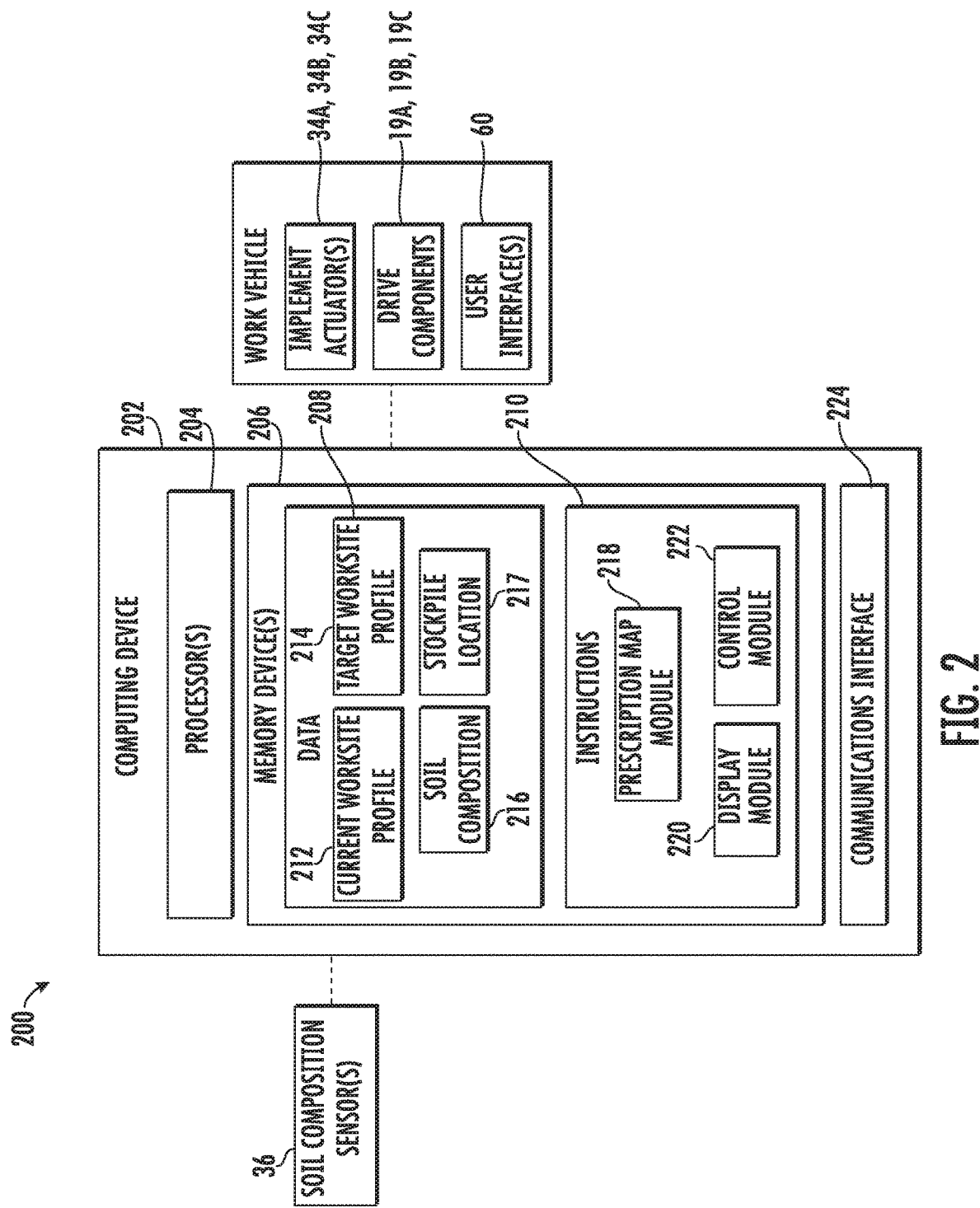
FIG. 2 illustrates a schematic view of one embodiment of a system for performing an earthmoving operation in accordance with aspects of the present subject matter.

Referring now to FIG. 2, a schematic view of one embodiment of a system 200 for performing an earthmoving operation is illustrated in accordance with aspects of the present subject matter. In general, the system 200 will be described herein with reference to the work vehicle 10 described above with reference to FIG. 1. However, it should be appreciated by those of ordinary skill in the art that the disclosed system 200 may generally be utilized with work vehicles having any suitable vehicle configuration. Additionally, it should be appreciated that, for purposes of illustration, communicative links or electrical couplings of the system 200 shown in FIG. 2 are indicated by dashed lines.

In several embodiments, the system 200 may include a computing system 202 and various other components configured to be communicatively coupled to and/or controlled by the computing system 202, such as a user interface (e.g., user interface 60) having one or more input devices, and/or various components of the work vehicle 10 (e.g., actuator(s) 34A, 34B, 34C and drive components 19A, 19B, 19C). The user interface 60 described herein may include, without limitation, any combination of input and/or output devices that allow an operator to provide operator inputs to the computing system 202 and/or that allow the computing system 202 to provide feedback to the operator, such as a keyboard, keypad, pointing device, buttons, knobs, touch sensitive screen, mobile device, audio input device, audio output device, and/or the like. Additionally, in some embodiments, the computing system 202 may be communicatively coupled to the sensors 36.

In general, the computing system 202 may correspond to any suitable processor-based device(s), such as a given controller or computing device or any combination of controllers or computing devices. Thus, as shown in FIG. 2, the computing system 202 may generally include one or more processor(s) 204 and associated memory device(s) 206 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 206 of the computing system 202 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 206 may generally be configured to store information accessible to the processor(s) 204, including data 208 that can be retrieved, manipulated, created and/or stored by the processor(s) 204 and instructions 210 that can be executed by the processor(s) 204.

It should be appreciated that the computing system 202 may correspond to an existing computing system for the work vehicle 10 or may correspond to a separate processing device. For instance, in one embodiment, the computing system 202 may form all or part of a separate plug-in module that may be installed in operative association with the work vehicle 10 to allow for the disclosed system and method to be implemented without requiring additional software to be uploaded onto existing control devices of the work vehicle 10.

In several embodiments, the data 208 may be stored in one or more databases. For example, the memory 206 may include a current worksite profile database 212 for storing an initial or current profile of the worksite, such as a topography map and/or utilities map of the worksite, received from an operator, the sensor(s) 36, and/or any other suitable source (e.g., an offsite server, separate database, separate computing device, etc.). For instance, data indicative of the current grade of and/or any known underground obstacles within the worksite may be received from the operator and/or from any other suitable source (e.g., by uploading a 3D map previously generated for the current worksite grade via the user interface 60) and/or from the sensor(s) 36. For example, the sensor(s) 36 may be configured to continuously or periodically capture data associated with a portion of the worksite, such as immediately before or at the start of the performance of an earthmoving operation, which may be used as an indicator of the initial grade or profile of the worksite. It should be appreciated that, as used herein, the data received from the sensor(s) 36 may include any suitable type of data that allows for the worksite to be analyzed, including radar data, and/or any other suitable data. The term current worksite data 212 may include any suitable data transmitted to the computing system 202 from the operator, the sensor(s) 36, and/or any other suitable source and stored within the current worksite database 212 for subsequent processing and/or analysis.

Further, the memory 206 may include a target worksite profile database 214 for storing data indicative of a target profile or grade of the worksite (e.g., trench dimensions and/or a 3D map generated for the target worksite grade). The data indicative of the target profile may be received from the operator via the user interface 60. However, the data indicative of the target grade of the worksite may be received from any other source, such as a separate database. The term target worksite data 214 may include any suitable data transmitted to the computing system 202 from the operator, and/or any other suitable source, and stored within the target worksite database 214 for subsequent processing and/or analysis.

Moreover, the memory 206 may include a soil composition database 216 for storing data indicative of the soil composition below a surface of the worksite, received from the sensor(s) 36. For instance, the sensor(s) 36 may be configured to continuously or periodically capture data associated with a portion of the worksite, such as immediately before or during the performance of an earthmoving operation, that is used as an indicator of the soil composition of the worksite, which is further indicative of different soil types, underground obstacles, and/or the like. It should be appreciated that, as used herein, the data received from the sensor(s) 36 may include any suitable type of data that allows for the worksite to be analyzed, including radar data, and/or any other suitable data. The term soil composition data 216 may include any suitable data transmitted to the computing system 202 from the sensor(s) 36, and/or any other suitable source, and stored within the soil composition database 216 for subsequent processing and/or analysis.

Additionally, the memory 206 may include a stockpile location database 217 for storing the data indicative of locations of stockpiles (e.g., coordinates) within the worksite for each soil type to be removed from the worksite. The stockpile location(s) may be received from the operator via the user interface 60. However, the data indicative of the stockpile location may be received from any other source, such as a separate database. The term stockpile location data 217 may include any suitable data transmitted to the computing system 202 from the operator, and/or any other suitable source, and stored within the stockpile location database 217 for subsequent processing and/or analysis.

Referring still to FIG. 2, in several embodiments, the instructions 210 stored within the memory 206 of the computing system 202 may be used by the processor 204 to implement an earthmoving prescription map module 218. In general, the earthmoving prescription map module 218 may be configured to analyze the soil composition data 216 deriving from the sensor(s) 36 along with at least one of the current worksite data 212 or the target worksite data 214 to generate an earthmoving prescription map for the worksite. For instance, as described above, the soil composition data 216 detected by the sensor(s) 36 may be used to identify the soil type at each position and depth within the sensed area of the worksite, as well as any underground obstacles. The soil earthmoving prescription map module 218 may then generate an earthmoving prescription map for the worksite indicating the transitions between the different soil composition layers and any underground obstacles between the surface of the worksite and the target profile of the worksite based at least in part on the target worksite data 214, the soil composition data 216, and optionally, the current worksite data 212. The earthmoving prescription map may further correlate a soil type for each soil composition layer detected by the sensor(s) 36 using a known correlation. Moreover, the earthmoving prescription map may prescribe one or more operational settings for the work vehicle corresponding to the soil type for each soil composition layer. For instance, the earthmoving prescription map may prescribe at least one of an engine speed of the engine 19A, a transmission gear ratio of the transmission 19B, a locking state of the differential 19C, or a maximum percentage fill of the bucket 20 for each soil type. In some embodiments, at least one of the engine speed of the engine 19A, the transmission gear ratio of the transmission 19B, the locking state of the differential 19C, or the maximum fill percentage of the bucket 20 prescribed differs between adjacent soil composition layers. Additionally, the earthmoving prescription map may prescribe a stockpile location corresponding to the soil type determined for each soil composition layer.

It should be appreciated that the sensor(s) 36 may collect data throughout an earthmoving operation such that the earthmoving prescription map module 218 may further be configured to update the earthmoving prescription map 250 the earthmoving operation is being performed. As such, a surface or current profile 254 of the worksite and the soil composition layers of the earthmoving prescription map 250 may be updated to show the progress of the earthmoving operation.

Figure 3:
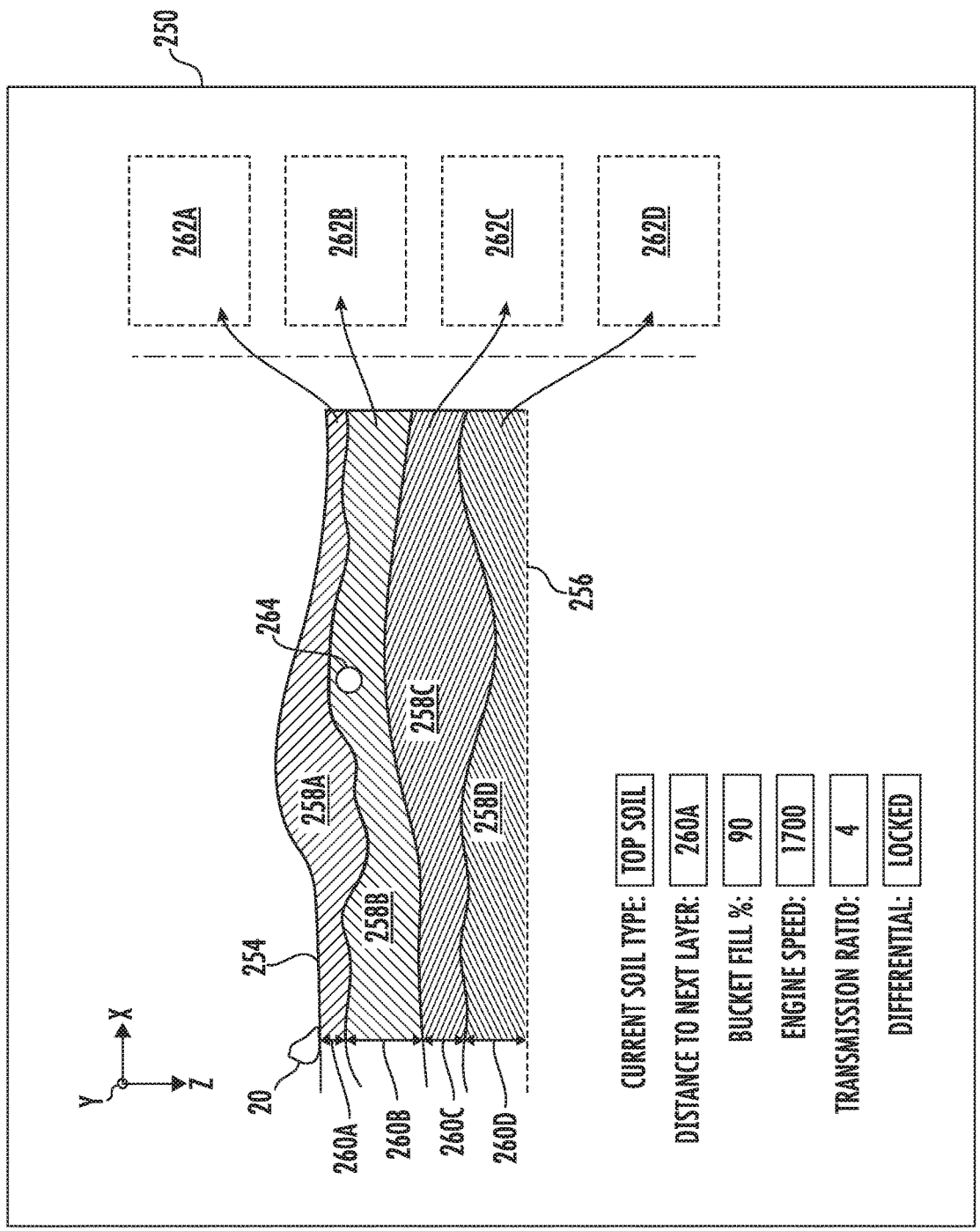
FIG. 3 illustrates a graphical view of an example earthmoving prescription map for performing an earthmoving operation that may be generated in accordance with aspects of the present subject matter.

Referring to FIG. 3, an example embodiment of a graphical view of an earthmoving prescription map 250 for performing an earthmoving operation is illustrated in accordance with aspects of the present subject matter. As shown in FIG. 3, the earthmoving prescription map 250 may include a section view of the worksite indicating the changes in soil composition between a surface profile 254 and a target profile 256 of the worksite based on data received from the soil composition sensor(s) 36 (FIGS. 1 and 2) and the operator, respectively. For example, the earthmoving prescription map 250 includes a first soil composition layer 258A, a second soil composition layer 258B, a third soil composition layer 258C, and a fourth soil composition layer 258D. Each soil composition layer 258 is generally associated with a different soil composition, which is indicative of a particular soil type, such as topsoil, clay, sand, rock, and/or the like, For example, the first soil composition layer 258A is associated with a first soil composition and type, the second soil composition layer 258B is associated with a second soil composition and type, the third soil composition layer 258C is associated with a third soil composition and type, and the fourth soil composition layer 258D is associated with a fourth soil composition and type. Adjacent soil composition layers 258 have different soil compositions, and therefore, types. For instance, the first and second soil compositions are different from each other. Similarly, the second and third soil compositions are different from each other, and the third and fourth soil compositions are different from each other.

Further, in some embodiments, the earthmoving prescription map 250 identifies the depth range (e.g., Z coordinates) across which each soil composition layer 258 extends for each position (e.g., X, Y coordinate location) within the worksite. For instance, as shown in FIG. 3, the depth ranges 260 for the soil composition layers 258 are provided for the current location of the bucket 20 within the worksite. For example, the first soil composition layer 258A extends across a first depth range 260A between the surface 254 of the worksite and the second soil composition layer 258B. The second soil composition layer 258B extends across a second depth range 260B, below the first soil composition layer 258A, particularly between the first and third soil composition layers 258A, 258C. The third soil composition layer 258C extends across a third depth range 260C, below the second composition layer 258B, particularly between the second and fourth soil composition layers 258B, 258D. Additionally, the fourth soil composition layer 258D extends across a fourth depth range 260D, below the third soil composition layer 258C, particularly between the third soil composition layer 258C and the target profile 256 of the worksite. Such depth ranges 260 may be used to determine the distance to the next soil composition layer 258.

Moreover, in some embodiments, the earthmoving prescription map 250 indicates an obstacle 264, such as a pipe, a wire, a tank, and/or the like. As described above, the obstacle 264 may be identified from the worksite profile data 212 received from an operator via the user interface 60 or another suitable source and/or from the soil composition data 216 received from the sensor(s) 36. When the obstacle 264 is identified using both the worksite profile data 212 and the soil composition data 216, the confidence in the accuracy of the worksite profile data 212 and/or soil composition data 216 may be increased.

As indicated above, in some embodiments, the earthmoving prescription map 250 suggests or prescribes at least one operational setting of the work vehicle 10 depending on the soil composition or type being worked. For instance, the earthmoving prescription map 250 may prescribe at least one of an engine speed of the engine 19A, a transmission gear ratio of the transmission 19B, whether the differential 19C should be locked or unlocked, or the maximum percentage that the bucket 20 should be filled for at least the current soil composition layer or type being worked. For example, topsoil may be easier to work than clay, as such, the engine speed may be lower, or a higher transmission gear ratio may be used when working topsoil than clay.

Additionally, as indicated above, in some embodiments, the earthmoving prescription map 250 identifies separate stockpiling locations 262 for each soil composition layer 258. For instance, as shown in FIG. 3, the earthmoving prescription map 250 identifies a first stockpile location 262A for depositing materials from the first soil composition layer 258A, a second stockpile location 262B for depositing materials from the second soil composition layer 258B, a third stockpile location 262C for depositing materials from the third soil composition layer 258C, and a fourth stockpile location 262D for depositing materials from the fourth soil composition layer 258D. As such, different soil types removed during an earthmoving operation may be kept separate for future uses.

Referring back to FIG. 2, in some embodiments, the instructions 210 stored within the memory 206 of the computing system 202 may be executed by the processor(s) to implement a display module 220. The display module 220 may generally be configured to control the user interface 60 to indicate to an operator at least one of a distance to the next soil composition layer or soil type, the current soil type being worked, a stockpile location, and/or an operational setting of the work vehicle. For example, the display module 220 may be configured to control a display screen of the user interface 60 to generate an augmented view of the worksite, such as to display the earthmoving prescription map 250 shown in FIG. 3, including the surface profile 254 of the worksite, the target profile 256 of the worksite, and the different soil composition layers 258 between the surface profile 254 and the target profile 256 of the worksite, and/or at least one of a distance to the next soil composition layer or soil type, the current soil type being worked, a stockpile location, and/or an operational setting of the work vehicle.

Additionally, the instructions 210 stored within the memory 206 of the computing system 202 may be executed by the processor(s) to implement a control module 222. The control module 222 may generally be configured to control the work vehicle 10 to automatically perform an earthmoving operation based on the earthmoving prescription map 250 (FIG. 3) generated by the earthmoving prescription map module 218. The control module 222 may more particularly be configured to control the operation of one or more components of the work vehicle 10, such as by controlling the operation of one or more of the actuators 34A, 34B, 34C to control the implement 20 and/or the operation of one or more of the drive components 19A, 19B, 19C, to perform an earthmoving operation based on the earthmoving prescription map. For instance, the control module 222 may monitor a position of the bucket 20 relative to the soil composition layers 258 (FIG. 3) identified by the earthmoving prescription map 250 (FIG. 3) and control the position of the bucket 20 (e.g., height and/or angle) to separately remove the soil composition layers 258. Further, the control module 222 may control the work vehicle 10 to deposit the removed worksite materials of a given soil type to a corresponding stockpile location 262. Moreover, the control module 222 may pre-emptively adjust the operation of one or more of the drive components 19A, 19B, 19C based to the soil type to be worked to improve the efficiency of the earthmoving operation.

Moreover, as shown in FIG. 2, the computing system 202 may also include a communications interface 224 to provide a means for the computing system 202 to communicate with any of the various other system components described herein. For instance, one or more communicative links or interfaces (e.g., one or more data buses) may be provided between the communications interface 224 and the user interface 60 to allow operator inputs to be received by the computing system 202 and/or to allow the computing system 202 to control the operation of one or more components of the user interface 60 to present the earthmoving prescription map (e.g., a distance to the next soil composition layer, a soil composition type of the current soil composition layer being worked, one or more prescribed operating settings for the current soil composition layer, and/or the like), and/or one or more indicators of the progress of the earthmoving operation to the operator. Similarly, one or more communicative links or interfaces (e.g., one or more data buses) may be provided between the communications interface 224 and the sensor(s) 36 to allow data transmitted from the sensor(s) 36 to be received by the computing system 202. Moreover, one or more communicative links or interfaces (e.g., one or more data buses) may be provided between the communications interface 224 and the implement actuator(s) 34A, 34B, 34C for allowing the computing system 202 to control the operation of one or more operations of the actuator(s) 34A, 34B, 34C. Additionally, one or more communicative links or interfaces (e.g., one or more data buses) may be provided between the communications interface 224 and the drive components 19A, 19B, 19C of the work vehicle for allowing the computing system 202 to control the operation of the drive components 19A, 19B, 19C.

Figure 4:
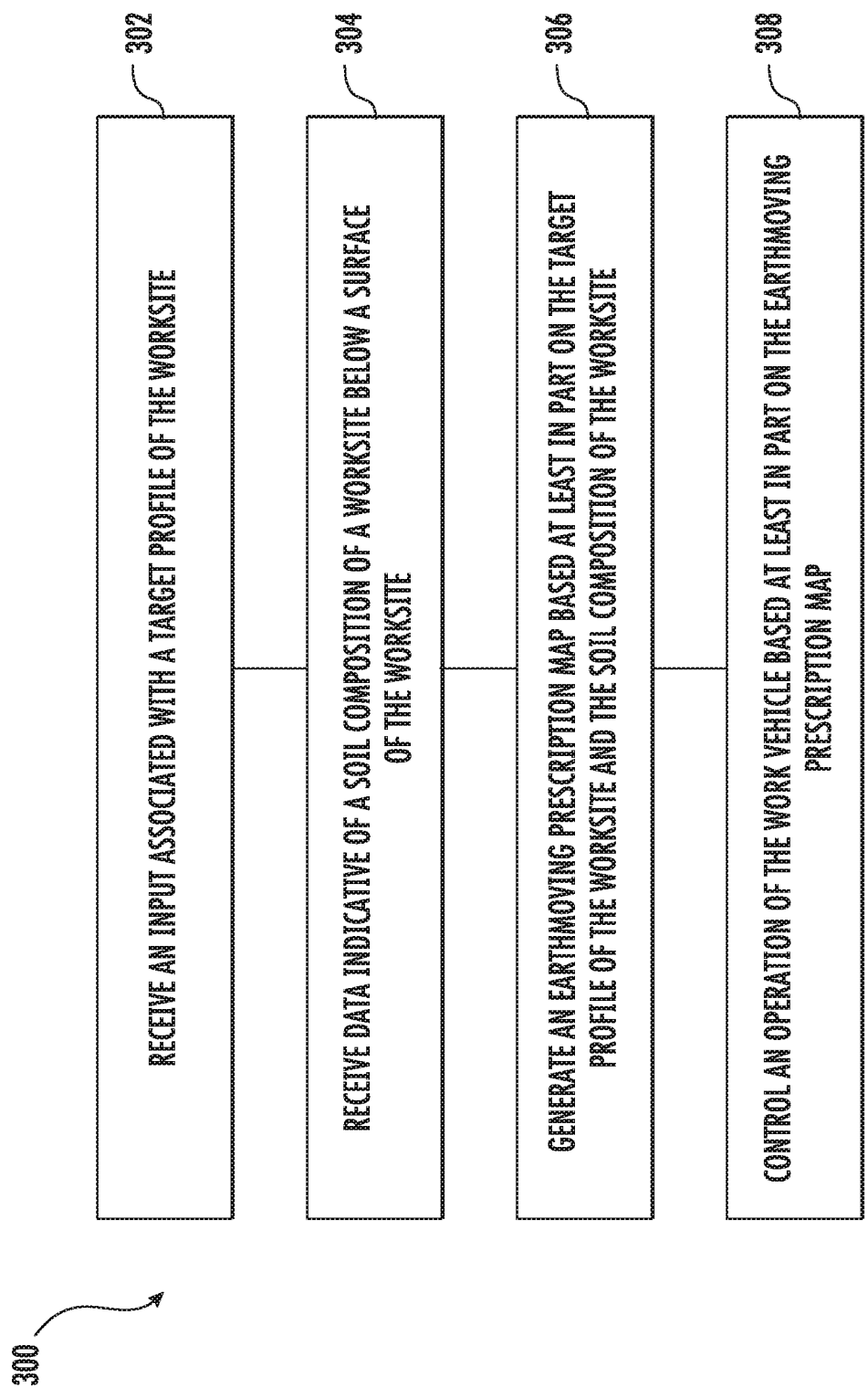
FIG. 4 illustrates a method for performing an earthmoving operation in accordance with aspects of the present subject matter.

Referring now to FIG. 4, a flow diagram of one embodiment of a method 300 for performing an earthmoving operation is illustrated in accordance with aspects of the present subject matter. In general, the method 300 will be described herein with reference to the work vehicle 10 shown in FIG. 1, as well as the various system components of the system 200 shown in FIG. 2. However, it should be appreciated that the disclosed method 300 may be implemented with work vehicles having any other suitable configurations, and/or within systems having any other suitable system configuration. In addition, although FIG. 4 depicts steps performed in a particular order for purposes of illustration and discussion, the method steps discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 4, at (302), the method 300 may include receiving an input associated with a target profile of the worksite. For instance, as indicated above, the computing system 202 may receive an input from an operator of the work vehicle 10 via a user interface (e.g., user interface 60) indicative of a target profile or grade 256 of the worksite.

Further, at (304), the method 300 may include receiving data indicative of a soil composition of a worksite below a surface of the worksite. For example, as described above, the computing system 202 may further receive data from the soil composition sensor(s) 36 indicative of the soil composition of the worksite below a surface of the worksite.

Moreover, at (306), the method 300 may include generating an earthmoving prescription map based at least in part on the target profile of the worksite and the soil composition of the worksite. For instance, as discussed above, the computing system 202 may generate an earthmoving prescription map 250 based at least in part on the target profile 256 of the worksite and the soil composition of the worksite. The earthmoving prescription map 250 generally indicates the soil composition layers 258 between the surface profile 254 of the worksite and the target profile 256 of the worksite.

Additionally, at (308), the method 300 may include controlling an operation of the work vehicle based at least in part on the earthmoving prescription map. For example, as indicated above, the computing system 202 may control the operation of the user interface 60 associated with the work vehicle 10 to indicate to an operator elements of the earthmoving prescription map 250 and/or one or more other components of the work vehicle 10, such as the implement actuators 34A, 34B, 34C and the drive components 19A, 19B, 19C, to automatically perform an earthmoving operation based on the earthmoving prescription map 250.

It is to be understood that the steps of the method 300 are performed by the computing system 202 upon loading and executing software code or instructions which are tangibly stored on a tangible computer readable medium, such as on a magnetic medium, e.g., a computer hard drive, an optical medium, e.g., an optical disk, solid-state memory, e.g., flash memory, or other storage media known in the art. Thus, any of the functionality performed by the computing system 202 described herein, such as the method 300, is implemented in software code or instructions which are tangibly stored on a tangible computer readable medium. The computing system 202 loads the software code or instructions via a direct interface with the computer readable medium or via a wired and/or wireless network. Upon loading and executing such software code or instructions by the computing system 202, the computing system 202 may perform any of the functionality of the computing system 202 described herein, including any steps of the method 300 described herein.

The term "software code" or "code" used herein refers to any instructions or set of instructions that influence the operation of a computer or computing system. They may exist in a computer-executable form, such as machine code, which is the set of instructions and data directly executed by a computer's central processing unit or by a computing system, a human-understandable form, such as source code, which may be compiled in order to be executed by a computer's central processing unit or by a computing system, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for performing an earthmoving operation with a work vehicle, the work vehicle having an articulable implement, the method comprising:
   receiving, with a computing device, an input associated with a target profile of a worksite;
   receiving, with the computing device, data indicative of a soil composition of a worksite below a surface of the worksite;
   generating, with the computing device, an earthmoving prescription map based at least in part on the target profile of the worksite and the soil composition of the worksite, the earthmoving prescription map indicating soil composition layers between the surface of the worksite and the target profile of the worksite; and
   controlling, with the computing device, an operation of the work vehicle to perform the earthmoving operation with the implement at the worksite based at least in part on the earthmoving prescription map.

2. The method of claim 1, wherein controlling the operation of the work vehicle to perform the earthmoving operation comprises controlling the operation of the work vehicle to remove worksite materials associated with a first soil composition layer of the soil composition layers with the implement separately from worksite materials associated with a second soil composition layer of the soil composition layers, the worksite materials associated with the second soil composition layer being different from the worksite materials associated with the first soil composition layer.

3. The method of claim 2, wherein the first soil composition layer extends across a first depth range below the surface of the worksite, and the second soil composition layer extends across a second depth range below the surface of the worksite, the second depth range being below the first depth range.

4. The method of claim 2, wherein controlling the operation of the work vehicle to perform the earthmoving operation comprises controlling the operation of the work vehicle to deposit the removed worksite materials associated with the first soil composition layer at a first stockpile location and to deposit the removed worksite materials associated with the second soil composition layer at a second stockpile location, the first and second stockpile locations being separate from one another.

5. The method of claim 2, wherein controlling the operation of the work vehicle to perform the earthmoving operation further comprises controlling the operation of the work vehicle to operate at a first operational setting when removing the worksite materials associated with the first soil composition layer and at a second operational setting when removing the worksite materials associated with the second soil composition layer.

6. The method of claim 5, wherein at least one of an engine speed, a transmission gear ratio, a differential locking state, or a maximum implement fill is different between the first and second operational settings.

7. The method of claim 1, further comprising controlling a user interface of the work vehicle to display the earthmoving prescription map.

8. The method of claim 1, further comprising controlling a user interface of the work vehicle to display at least one of a prescribed operational setting of the work vehicle for working a current one of the soil composition layers, a prescribed worksite location for depositing materials removed from the current one of the soil composition layers, or a distance between the implement and a subsequent one of the soil composition layers directly adjacent to the current one of the soil composition layers.

9. The method of claim 1, further comprising receiving, with the computing device, an input associated with a current profile of the worksite, the current profile being associated with a topography of the worksite,
wherein generating the earthmoving prescription map comprises generating the earthmoving prescription map based at least on part on the current profile of the worksite, the target profile of the worksite, and the soil composition of the worksite.

10. The method of claim 1, further comprising updating, with the computing device, the earthmoving prescription map while controlling the work vehicle to perform the earthmoving operation.

11. A system for performing an earthmoving operation, comprising:
a work vehicle having an articulable implement;
a soil composition sensor supported on the work vehicle, the soil composition sensor being configured to generate data indicative of a soil composition below a surface of a worksite; and
a computing system communicatively coupled to the soil composition sensor and the work vehicle, the computing system being configured to:
receive an input associated with a target profile of the worksite;
receive the data indicative of the soil composition of the worksite; and
generate an earthmoving prescription map based at least in part on the target profile of the worksite and the soil composition of the worksite, the earthmoving prescription map indicating soil composition layers between the surface of the worksite and the target profile of the worksite.

12. The system of claim 11, wherein the computing system is further configured to automatically control an operation of the work vehicle to perform the earthmoving operation at the worksite based at least in part on the earthmoving prescription map.

13. The system of claim 12, wherein controlling the operation of the work vehicle to perform the earthmoving operation comprises controlling the operation of the work vehicle to remove with the implement worksite materials associated with a first soil composition layer of the soil composition layers with the implement separately from worksite materials associated with a second soil composition layer of the soil composition layers, the worksite materials associated with the second soil composition layer being different from the worksite materials associated with the first soil composition layer.

14. The system of claim 13, wherein the first soil composition layer extends across a first depth range below the surface of the worksite, and the second soil composition layer extends across a second depth range below the surface of the worksite, the second depth range being below the first depth range.

15. The system of claim 13, wherein the computing system controls the work vehicle to operate at a first operational setting when removing the worksite materials associated with the first soil composition layer and at a second operational setting when removing the worksite materials associated with the second soil composition layer.

16. The system of claim 15, wherein at least one of an engine speed, a transmission gear ratio, a differential locking state, or a maximum implement fill is different between the first and second operational settings.

17. The system of claim 11, further comprising a user interface, wherein the computing system is further configured to control the operation of the user interface to display the earthmoving prescription map.

18. The system of claim 11, further comprising a user interface, wherein the computing system is further configured to control the operation of the user interface to display at least one of a prescribed operational setting of the work vehicle for working a current one of the soil composition layers, a prescribed worksite location for depositing materials removed from the current one of the soil composition layers, or a distance between the implement and a subsequent one of the soil composition layers directly adjacent to the current one of the soil composition layers based at least in part on the earthmoving prescription map.

19. The system of claim 11, wherein the soil composition sensor comprises a ground penetrating radar.

20. The method of claim 1, wherein controlling the operation of the work vehicle to perform the earthmoving operation comprises automatically controlling the operation of the work vehicle to perform the earthmoving operation with the implement at the worksite to separate the different soil composition layers based at least in part on the earthmoving prescription map.

\* \* \* \* \*